United States Patent
Hung et al.

(10) Patent No.: US 6,852,483 B1
(45) Date of Patent: Feb. 8, 2005

(54) PREDICTING SURVIVAL OF PATIENTS WITH SQUAMOUS CELL CARCINOMA

(75) Inventors: Mien-chie Hung, Houston, TX (US); Weiya Xia, Missouri City, TX (US); Yiu-Keung Lau, Houston, TX (US)

(73) Assignee: Kuo Kwang Biotech Corporation, Taichung (TW)

( * ) Notice: Subject to any disclaimer, the term of this patent is extended or adjusted under 35 U.S.C. 154(b) by 179 days.

(21) Appl. No.: 09/637,190

(22) Filed: Aug. 11, 2000

(51) Int. Cl.[7] .................. G01N 33/50; G01N 33/53; C12Q 1/68
(52) U.S. Cl. .................. 435/4; 435/6; 435/7.1; 435/7.2; 435/7.23; 436/64
(58) Field of Search .............. 435/4, 6, 7.1, 7.2, 435/7.23; 436/64

(56) References Cited

U.S. PATENT DOCUMENTS

| | | | |
|---|---|---|---|
| 5,470,970 A | 11/1995 | Sager et al. | 536/23.5 |
| 5,801,001 A | 9/1998 | Sager et al. | 435/7.23 |
| 5,905,023 A | 5/1999 | Sager et al. | 435/6 |
| 5,932,210 A * | 8/1999 | Gregory et al. | |
| 6,197,754 B1 * | 3/2001 | Hung et al. | |

OTHER PUBLICATIONS

Ding et al, "Differential expression of maspin protein in human adenocarcinomas and squamous cell carcinomas", Proceeding of the American Association of Cancer Research, 1996, vol. 37, p. 90.*
Petrovich et al (Radiology, 1982, vol. 144, pp. 905–908), abstract.*
Weber et al (Otolaryngology–Head and Neck Surgery, 1988, vol. 99, pp. 16–23), abstract.*
Tytor et al (Clinical Otolaryngology, 1990, vol. 15, pp. 235–252), abstract.*
Eiband et al (American Journal of Surgery, 1989, vol. 158, pp. 314–317), abstract.*
Huwer et al (European Journal of Cardio–Thoracic Surgery, 1992, vol. 6, pp. 498–502), abstract.*
Nagel et al (Zentralblatt fur Chirurgie, 1994, vol. 119, pp. 225–232), abstract.*
van der Velden et al (Cancer, 1995, vol. 75, pp. 2885–2890), abstract.*
abstracts of Ding et al (Proc Amer Assoc Cancer Res, 1996, vol. 37, p. 90).*
Rheinwald et al (Cancer Research, 1981, vol. 41, pp. 1657–1663).*
Pemberton et al, Journal of Histochemistry and Cytochemistry, 1997, vol. 45, pp. 1697–1706.*
Xia et al., "High tumoral maspin . . . ," Oncogene, 19(20):2398–2403, 2000.
Pemberton et al., "Maspin Is an . . . ," The Journal of Histochemistry & Cytochemistry, 45(12):1697–1706, 1997.
Sager et al., "Maspin: A Tumor . . . ," Current Topics in Microbiology 213/I and Immunology, 51–64.
Sheng et al., "Production, Purification . . . ," The Journal of Biological Chemistry, 269(49):30988–30993, 1994.
Zhang et al., "Transactivation through . . . ," Cell Growth & Differentiation, 8:179–186, 1997.

(List continued on next page.)

Primary Examiner—Karen A. Canella
(74) Attorney, Agent, or Firm—Fish & Richardson P.C.

(57) ABSTRACT

The invention relates to methods of determining a relative probability of survival for a subject with squamous cell carcinoma by obtaining a biological sample from a subject with squamous cell carcinoma; detecting a level of maspin gene expression in the biological sample; and comparing the level with a threshold level of maspin gene expression. A level of maspin gene expression in the biological sample above the threshold level indicates a relatively high probability of survival, or a level of maspin gene expression in the biological sample below the threshold level indicates a relatively low probability of survival.

20 Claims, 1 Drawing Sheet

OTHER PUBLICATIONS

Zou et al., "Maspin, a Serpin . . . ," Science, 263:526–580, 1994.

Zhang et al., "Expression of a . . . ," Proc. Natl. Acad. Sci. USA, 94:5673–5678, 1997.

Xia et al., "High Tumor Maspin . . . ," Abstract No. 4381, 91st Annual Meeting for AAC in San Francisco on Apr. 1–5, 2000, Proceedings of the American Association for Cancer Research, 41:689, 2000.

* cited by examiner

PREDICTING SURVIVAL OF PATIENTS WITH SQUAMOUS CELL CARCINOMA

BACKGROUND OF THE INVENTION

Maspin is a 42 kDa protein that belongs to the serpin family of protease inhibitors. As a cytoplasmic protein, maspin associates with secretory vesicles and the cell surface (Pemberton et al., J. Histochem. Cytochem 45:1697–1706, 1997) and is expressed in normal human mammary epithelia cells (Zou et al., Science 263:526–529, 1994).

SUMMARY OF THE INVENTION

The invention is based on the discovery that the level of maspin gene expression in patients with squamous cell carcinoma (SCC) positively correlates with the relative probability of survival for those patients. In addition, it has been discovered that the presence of cancerous cells in the lymph nodes of a squamous cell carcinoma patient is also positively correlated with maspin gene expression. Thus, maspin gene expression can predict the relative probability of survival as well as whether lymph node metastasis has occurred in these patients.

Accordingly, the invention features a method of determining a relative probability of survival for a subject (e.g., a human patient) with squamous cell carcinoma by determining a level of maspin gene expression in a biological sample from a subject with squamous cell carcinoma; and comparing the level with a threshold level of maspin gene expression. A level of maspin gene expression in the biological sample above a threshold level indicates a relatively high probability of survival, or a level of maspin gene expression in the biological sample below a threshold level indicates a relatively low probability of survival. The low or high probability is relative to the probability associated with the threshold level of gene expression.

The invention also features a method of determining whether a subject (e.g., a human patient) with squamous cell carcinoma has a lymph node containing cancerous cells by determining a level of maspin gene expression in a biological sample from a subject with squamous cell carcinoma; and comparing the level with a threshold level of maspin gene expression. A level of maspin gene expression in the biological sample above a threshold level indicates that the subject does not have a lymph node containing cancerous cells, and a level of maspin gene expression in the biological sample below a threshold level indicates that the subject has a lymph node containing cancerous cells.

The maspin expression threshold levels can be determined empirically, as described in the working example below. For instance, the threshold level can be the level at which greater than 70% (e.g., 75, 80, 85, 90, or 95%) of patients survive for at least 50 months (e.g., at least 60, 70, 80, 90, 150, or 200 months). These levels are determined by segregating a population of SCC patients with a continuum of maspin expression levels into discrete groups based on maspin expression, then determining the survival curve for each group. The threshold levels of expression for exclusion or inclusion in any group are set to achieve predetermined levels of survival.

When practicing a method of the invention, the level of maspin gene expression can be determined by an amount of maspin protein in the biological sample, and the threshold level can be an amount of maspin protein. Maspin protein amounts can be determined using any suitable assay, such as by using an anti-maspin antibody, e.g., in a Western blot or a immunohistochemical method. Alternatively, the level of maspin gene expression can be determined by an amount of a maspin mRNA in the biological sample, and the threshold level can be an amount of the maspin mRNA. Since the nucleotide sequence of the maspin cDNA is known (see, e.g. U.S. Pat. No. 5,905,023), maspin mRNA amounts can be readily determined using any suitable assay, such as Northern blotting, RT-PCR, or on biochips. Biological samples appropriate for use in the methods of the invention include solid tissue samples from tumors of the tongue, cheek, floor of the mouth, gum, lip mucosa, palate, mucosa of the mandibular/molar area, and mandible. In short, any biological sample from a subject that is suspected of containing maspin protein or nucleic acid can be used.

The methods of the invention provide a means of predicting the chances of survival and lymph node involvement in squamous cell carcinoma patients. Thus, the invention offers prognostic information to the patient and his or her health care provider to ensure better informed medical decisions. Maspin expression can also be used to predict cancer patient survival in general, i.e., in addition to squamous cell carcinoma, the methods can be applied to other cancer types.

Other features or advantages of the present invention will be apparent from the following detailed description, and also from the claims.

DETAILED DESCRIPTION

Figure 1:
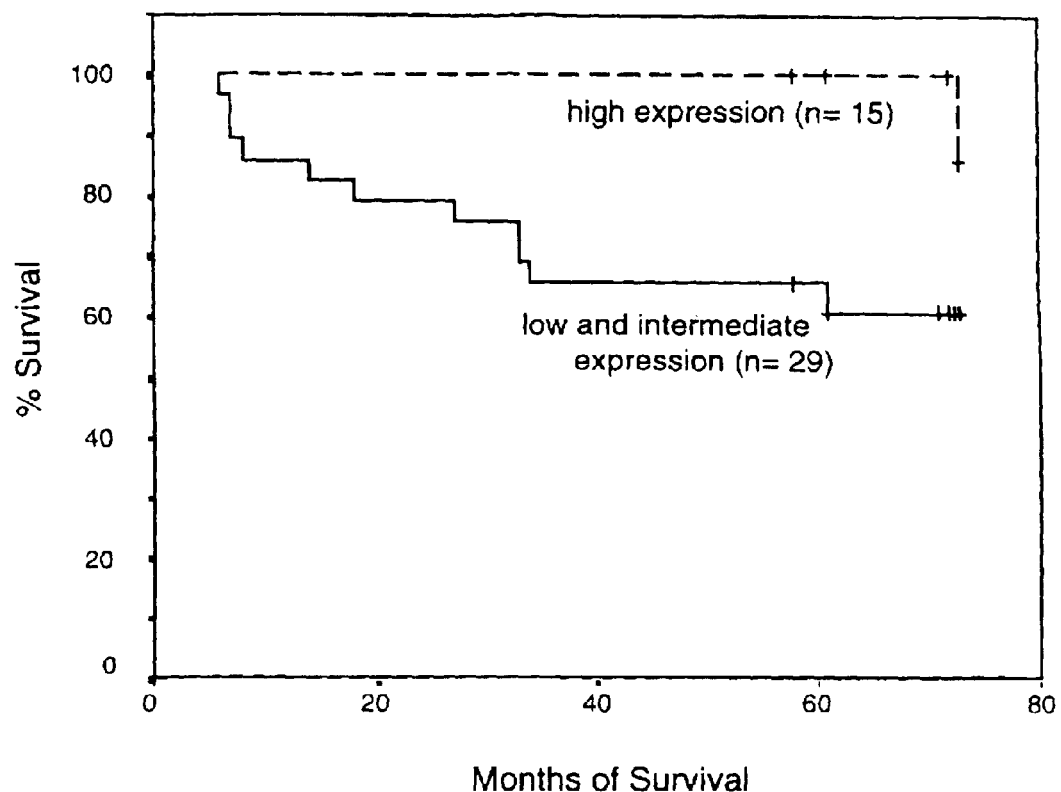
FIG. 1 is a graph of time (in months) versus percent of squamous cell carcinoma patients surviving after specified times.

The invention relates to predictive medicine using maspin gene expression as a determinant of survival and lymph node involvement in squamous cell carcinoma patients. Contemplated within the scope of this invention is the implementation of maspin gene expression analysis as a part of a pharmacogenetic protocol (e.g. using biochips) for evaluating patient status and prognosis.

The level of mRNA corresponding to the maspin gene in a cell can be determined by in situ or in vitro formats.

The maspin mRNA probes can be used in hybridization or amplification assays that include, but are not limited to, Southern or Northern analyses, polymerase chain reaction analyses and probe arrays. One diagnostic method for the detection of mRNA levels involves contacting the mRNA with a nucleic acid molecule (probe) that can hybridize to the mRNA encoded by the gene being detected. The nucleic acid probe can be, for example, a full-length maspin nucleic acid or a portion thereof, such as an oligonucleotide of at least 7, 15, 30, 50, 100, 250 or 500 nucleotides in length and sufficient to specifically hybridize under stringent conditions to maspin mRNA or cDNA.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the maspin gene.

The level of mRNA in a sample that is encoded by a maspin nucleic acid can be evaluated with nucleic acid amplification, e.g., by RT-PCR (U.S. Pat. No. 4,683,202), ligase chain reaction (Barany, Proc. Natl. Acad. Sci. USA 88:189–193, 1991), self sustained sequence replication (Guatelli et al., Proc. Natl. Acad. Sci. USA 87:1874–1878, 1990), transcriptional amplification system (Kwoh et al., Proc. Natl. Acad. Sci. USA 86:1173–1177, 1989), Q-Beta Replicase (Lizardi et al., Bio/Technology 6:1197, 1988), rolling circle replication (U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule including the nucleotide sequence flanked by the primers.

For in situ methods, a cell or tissue sample can be prepared/processed and immobilized on a support, typically a glass slide, and then contacted with a probe that can hybridize to mRNA that encodes the maspin gene being analyzed.

In another embodiment, the methods further include contacting a control sample with a compound or agent capable of detecting maspin mRNA, or cDNA, and comparing the presence of maspin mRNA or cDNA in the control sample with the presence of maspin mRNA or cDNA in the test sample.

A variety of methods can be used to determine the level of protein encoded by the maspin gene. In general, these methods include contacting an agent that selectively binds to the protein, such as an antibody, with a sample to evaluate the level of protein in the sample. In one embodiment, the antibody bears a detectable label. Antibodies can be polyclonal or monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance.

The detection methods can be used to detect maspin protein in a biological sample in vitro as well as in vivo. In vitro techniques for detection of maspin protein include enzyme linked immunosorbent assays (ELISAs), immunoprecipitations, immunofluorescence, enzyme immunoassays (EIA), radioimmunoassays (RIA), and Western blot analysis. In vivo techniques for detection of maspin protein include introducing into a subject a labeled anti-maspin antibody. For example, the antibody can be labeled with a radioactive marker whose presence and location in a subject can be detected by standard imaging techniques.

In another embodiment, the methods further include contacting the control sample with a compound or agent capable of detecting maspin protein, and comparing the presence of maspin protein in the control sample with the presence of maspin protein in the test sample.

Without further elaboration, it is believed that one skilled in the art can, based on the above disclosure and the example described below, utilize the present invention to its fullest extent. The following example is to be construed as merely illustrative of how one skilled in the art can implement the invention, and is not limitative of the remainder of the disclosure in any way. Any publications cited in this disclosure are hereby incorporated by reference.

Materials and Methods

Patients and specimens. Forty-four specimens of prim oral squamous cell carcinoma (SCC) were obtained from the Department of Oral Pathology, Ninth People's Hospital, Second Medical University, Shanghai, People's Republic of China. The patients from whom these samples were excised (29 men and 15 women) underwent surgical treatment in that hospital between 1989 and 1990. Their ages ranged from 32 to 74 years old (median=50 years old). The primary tumors were graded according to the WHO classification as described in Xia et al., Clin. Cancer Res. 3:3–9, 1997. Of the 44 cases, 34 were defined as grade I and 10 as grade II. The tumor tissues included tongue (25 cases), cheek (2 cases), floor of the mouth (6 cases), gum (5 cases), lip mucosa (2 cases), palate (2 cases), mucosa of the mandibular/molar area (1 case), and mandible (1 case). The specimens were fixed in formalin and embedded in paraffin. After surgical treatment, the 44 patients were followed for 3 to 6 months, either at the University Hospital clinic, or local clinics if the patients were not from the city. If a patient was found to have a recurrent disease in a local clinic, he or she would be referred back to the University Hospital. A questionnaire was sent to each patient to obtain information regarding general well-being, whether the patient had gone to a follow-up visit, what kind of treatment the patient received in his or her local clinic after an operation, and whether the patient was still alive. The patient were followed for a period of more than 6 years.

Two patients received chemotherapy, and two patients received radiation therapy after surgery. Thirty-six patients did not receive any post-surgical treatment, and data for four patients were not available. The median survival rate for these 44 patients was 61 months (ranging from 6 to 73 months). A total of 11 patients died during the study period. Ten of the patients died from primary tumors, and one died of lung metastasis from a primary tumor.

Immunohistochemical staining. A modified immunoperoxidase staining method was used as described in Xia et al., supra. Tissue sections were deparaffinized and dehydrated in a graded series of alcohol. The sections were then digested in 0.05% trypsin for 15 minutes, blocked in 0.3% hydrogen peroxide in methanol for 15 minutes, and treated with 1% (v/v) normal goat serum for 30 minutes. The slides were incubated with AbS4A purified maspin polyclonal antibody (10 μg/ml) for 3 hours at room temperature; the antibody is described in Sheng et al., Proc. Natl. Acad. Sci. USA 93:11669–11674, 1996. After extensive washing with PBS, the slides were incubated for another 30 minutes at room temperature with the biotinylated goat anti-rabbit IgG antibody diluted 1:200 in PBS. The slides were then incubated for 60 minutes at room temperature with an avidin-biotin-peroxidase complex diluted 1:100 in PBS. The peroxidase-catalyzed product was visualized with 0.125% aminoethyl-carbazole chromogen stock solution (Sigma Chemical Co.). Between steps, the slides were rinsed for 2 minutes in PBS three times.

After light counterstaining with the Mayer's modified hematoxylin (Sigma Chemical Co.), the slides were dehydrated and mounted. Negative controls, in which PBS was used instead of the primary antibody, were examined with each batch of slides stained. A section of normal oral epithelium previously identified as strongly staining was used as a positive control. Consistency within and between assays was maintained by including these positive and negative controls with each batch of slides stained. The prepared slides were examined by light microscopy. Those tumor cells that were immunostained with red granules were considered positive, and those cells without any immunostaining were considered negative. Cytoplasmic, but not membrane, staining was observed. Maspin immunoreactivity was ranked into three groups according to the percentage and staining intensity of the positive tumor cells: high, greater than or equal to 50% cells stained; intermediate, 20–49% cells stained; or low, up to 20% cells stained. In general, the percentage of the stained cells positively correlated with the intensity of staining.

Cell culture. The seven head and neck squamous cell lines examined, including three oral squamous cell lines (Tu 138, 686/LN-1, and Tu 167), are described in Xia et al., supra. Human oral keratinocytes were used as a positive control. The head and neck SCC cell lines were grown in DMEM/F12 (Life Technologies, Inc., Grand Island, N.Y.) supplemented with 10% fetal bovine serum (FBS) and antibiotics. The human oral keratinocytes were maintained in DMEM/F12 supplemented with 10% FBS, 400 ng/ml hydrocortisone, 0.1 nM cholera toxin, 10 ng/ml epidermal growth factor, 0.089 mM adenine, 5 ng/ml insulin, and 100 IU/ml penicillin-streptomycin. Cells were maintained in a humidified incubator at 37° C. under 5% $CO_2$ in air.

Western blot analysis. Western blot analysis was performed to detect maspin expression in the head and neck SCC cell lines. Proteins were extracted by RIPA lysis buffer (20 mM $Na_2PO_4$ [pH 7.4], 150 mM NaCl, 1% Triton X-100, 1% aprotinin, 1 mM phenylmethylsulfonyl fluoride, 100 mM NaF, and 2 mM $Na_3VO_4$). Protein concentration was determined using a protein assay kit (Bio-Rad Laboratories, Hercules, Calif.) with control standards. Equal amounts (75 $\mu$g) of total protein from each sample were subjected to SDS-polyacrylamide gel electrophoresis and transferred to a nitrocellulose membrane. The membrane was blocked with 5% non-fat dry milk in PBS containing 0.1% (v/v) Tween 20 for 1 hour and then incubated 4° C. overnight with the purified AbS4A maspin polyclona antibody (1 mg/ml) or an actin antibody for controlling loading variability. The membranes were then incubated with the horseradish peroxidase-conjugated goat anti-rabbit IgG (1:5,000 dilution) or goat anti-mouse IgG (1:5,000 dilution) (Jackson ImmunoResearch Laboratories, Inc., West Grove, Pa.) for about 30 minutes at room temperature. The substrate produced by the secondary antibodies was detected using the enhanced chemiluminescence (ECL) system (Amersham Pharmacia Biotech).

Northern blot analysis. Total RNA was isolated from the cells or tissues using Trizol reagent (Life Technologies, Gaithersburg, Md.) or the Micro RNA Isolation Kit (Stratagene) according to the manufacturers' protocols. Equal amounts (25 mg) of total RNA were sized-fractionated on a 1% agarose gel containing formaldehyde. The RNA was then transferred to a nylon membrane and hybridized with a $^{32}$P-labeled probe produced from a 1 kb fragment of maspin cDNA using standard methods.

Statistical analysis. Fisher's exact test was used to analyze the association of maspin expression with clinicopathological factors such as age, sex, histological grade, tumor/lymph node/metastasis (TNM) stage, and subsequent treatment after surgery. The patients with low to intermediate maspin expression (i.e., lower than the normal level) were grouped together to perform a valid Fisher's exact test. Suvival cures (high vs. low and intermediate) were calculated using the Kaplan-Meier product limit estimate. The log-rank method was used to analyze differences in the survival time. The statistical analyses were performed by using SPSS software. Ap value of less than 0.05 was set as the criterion for statistical significance.

Results

Expression of maspin in oral SCC. To examine the expression pattern of maspin in the seven head and neck SCC cell lines, the maspin protein levels in each cell line were determined using Western blot analysis. Six of the seven lines tested, including all three oral SCC cell lines, expressed low to no maspin, in comparison to the positive control, normal human oral keratinocytes.

Next, the maspin mRNA levels in these cell lines were examined by Northern blot analysis. Most of the cell lines were found to express two forms of maspin mRNA. Two different maspin mRNA transcripts were also previously reported in human myoepithelial cells (Sternlicht et al., Clin. Cancer Res. 3:1949–1958, 1997). It was noted that the lower maspin mRNA band was correlated with maspin protein levels detectedby Western blotting analysis, far more than the upper maspin mRNA band, suggesting that the lower maspin mRNA band may be the functional mRNA and that the upper maspin mRNA band may be a less translatable or a precursor form of the functional maspin mRNA.

Maspin expression in the 44 oral SCC patient specimens was determined using a immunohistochemical technique. Normal oral epithelial tissue taken from gingiva was used as a positive control. Of 44 patient specimens examined, 29 (66%) expressed low or intermediate levels of maspin. The tumor cells in both the low and intermediate subgroups exhibited substantially weaker straining than that of the normal control tissue. The remaining 15 patient specimens (34%) expressed high levels of maspin, and the tumor cells in these samples stained as strongly as the normal control tissue.

Higher maspin expression is associated with the absence of lymph node metastasis. The association of maspin with other clinicopathological features, e g., patient age, patient sex, histological grade, TNM stage, and postsurgical treatment was examined in the 44 oral SCC patients, A significant positive association with the presence of lymph node involvement (p=0.009; Table 1) was observed.

TABLE 1

| | Maspin expression level | | |
|---|---|---|---|
| | low and intermediate[a] | high | p value[b] |
| Patients' sex | | | |
| Men | 20 | 9 | 0.74 |
| Women | 9 | 6 | |
| Age | | | |
| <50 years old | 11 | 10 | 0.11 |
| ≧50 years old | 18 | | |
| Histological Grade | | | |
| I | 21 | 13 | 0.45 |
| II | 8 | 2 | |
| Tumor Size | | | |
| $T_{1-2}$ | 27 | 14 | 1.0 |
| $T_3$ | 2 | 1 | |

TABLE 1-continued

| | Maspin expression level | | |
|---|---|---|---|
| | low and intermediate[a] | high | p value[b] |
| Nodal Stage | | | |
| No | 19 | 15 | 0.009 |
| Yes | 10 | 0 | |
| Distant Metastasis | | | |
| No | 21 | 13 | 0.45 |
| Yes | 8 | 2 | |
| Post-surgical Therapy[c] | | | |
| No | 22 | 14 | 0.28 |
| Yes | 4 | 0 | |

[a]Patients with low and intermediate level (i.e., lower than normal level) were grouped together to perform a valid Fisher's exact test.
[b]p value was obtained by Fisher's exact test
[c]Of the 44 Patients, two received chemotherapy, and two had radiotherapy after surgery. Data was not available for four patients, and the remaining 36 patients did not received any post surgical chemotherapy or radiotherapy.

In addition, all of the patients who expressed high levels of maspin did not show any nodal involvement, indicating that higher maspin expression was associated with the absence of lymph node metastasis.

Higher maspin expression is associated with longer survival. When the follow-up data for each patient was matched to maspin expression, as shown in FIG. 1, the patient population exhibiting high maspin expression levels survived far longer than the patient population exhibiting low or intermediate maspin expression levels p=0.017). These results suggest that high maspin expression in patients with oral SCC is a prognostic marker for long survival.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of determining a relative probability of survival for a subject with squamous cell carcinoma, the method comprising:
   determining a level of maspin gene expression in a biological sample from a subject with squamous cell carcinoma; and
   comparing the level with a threshold level of maspin gene expression, wherein a level of maspin gene expression in the biological sample above the threshold level indicates a relatively high probability of survival, wherein the threshold level is the level at which greater than 70% patients survive for at least 50 months.

2. The method of claim 1, wherein the level of maspin gene expression is determined by an amount of maspin protein in the biological sample, and the threshold level is an amount of maspin protein.

3. The method of claim 2, wherein the amount of maspin protein in the biological sample is determined using an antibody that specifically binds to maspin.

4. The method of claim 1, wherein the level of maspin gene expression is determined by an amount of a maspin mRNA in the biological sample, and the threshold level is an amount of the maspin mRNA.

5. The method of claim 4, wherein the amount of the maspin mRNA in the biological sample is determined by Northern blotting.

6. A method of determining a relative probability of survival for a subject with squamous cell carcinoma, the method comprising:
   determining a level of maspin gene expression in a biological sample from a subject with squamous cell carcinoma; and
   comparing the level with a threshold level of maspin gene expression, wherein a level of maspin gene expression in the biological sample below the threshold level indicates a relatively low probability of survival, wherein the threshold level is the level at which 70% patients survive for 50 months.

7. The method of claim 6, wherein the level of maspin gene expression is determined by an amount of maspin protein in the biological sample, and the threshold level is an amount of maspin protein.

8. The method of claim 7, wherein the amount of maspin protein in the biological sample is determined using an antibody that specifically binds to maspin.

9. The method of claim 6, wherein the level of maspin gene expression is determined by an amount of a maspin mRNA in the biological sample, and the threshold level is an amount of the maspin mRNA.

10. The method of claim 9, wherein the amount of the maspin mRNA in the biological sample is determined by Northern blotting.

11. A method of determining whether a subject with squamous cell carcinoma does not have a lymph node containing cancerous cells, the method comprising:
    determining a level of maspin gene expression in a biological sample from a subject with squamous cell carcinoma; and
    comparing the level with a threshold level of maspin gene expression, wherein a level of maspin gene expression in the biological sample above the threshold level indicates that the subject does not have a lymph node containing cancerous cells, wherein the threshold level is the level at which greater than 70% patients survive for at least 50 months.

12. The method of claim 11, wherein the level of maspin gene expression is determined by an amount of maspin protein in the biological sample, and the threshold level is an amount of maspin protein.

13. The method of claim 12, wherein the amount of maspin protein in the biological sample is determined using an antibody that specifically binds to maspin.

14. The method of claim 11, wherein the level of maspin gene expression is determined by an amount of a maspin mRNA in the biological sample, and the threshold level is an amount of the maspin mRNA.

15. The method of claim 14, wherein the amount of the maspin mRNA in the biological sample is determined by Northern blotting.

16. A method of determining whether a subject with squamous cell carcinoma has a lymph node containing cancerous cells, the method comprising:
    determining a level of maspin gene expression in a biological sample from a subject with squamous cell carcinoma; and
    comparing the level with a threshold level of maspin gene expression, wherein a level of maspin gene expression in the biological sample below the threshold level indicates that the subject has a lymph node containing cancerous cells, wherein the threshold level is the level at which 70% patients survive for 50 months.

17. The method of claim 16, wherein the level of maspin gene expression is determined by an amount of maspin protein in the biological sample, and the threshold level is an amount of maspin protein.

18. The method of claim 17, wherein the amount of maspin protein in the biological sample is determined using an antibody that specifically binds to maspin.

19. The method of claim 16, wherein the level of maspin gene expression is determined by an amount of a maspin mRNA in the biological sample, and the threshold level is an amount of the maspin mRNA.

20. The method of claim 19, wherein the amount of the maspin mRNA in the biological sample is determined by Northern blotting.

* * * * *